(12) United States Patent
Khwaja et al.

(10) Patent No.: US 10,874,309 B2
(45) Date of Patent: Dec. 29, 2020

(54) DETERMINING EMOTIONS USING CAMERA-BASED SENSING

(71) Applicant: Samsung Electronics Company, Ltd., Suwon-si (KR)

(72) Inventors: Ayesha Khwaja, Stanford, CA (US); James Young, Menlo Park, CA (US); Cody Wortham, Mountain View, CA (US); Sajid Sadi, Mountain View, CA (US); Jawahar Jain, Los Altos, CA (US)

(73) Assignee: Samsung Electronics Company, Ltd., Suwon (KR)

(*) Notice: Subject to any disclaimer, the term of this patent is extended or adjusted under 35 U.S.C. 154(b) by 245 days.

(21) Appl. No.: 15/951,068

(22) Filed: Apr. 11, 2018

(65) Prior Publication Data

US 2018/0314879 A1  Nov. 1, 2018

Related U.S. Application Data

(60) Provisional application No. 62/500,277, filed on May 2, 2017, provisional application No. 62/492,838, filed
(Continued)

(51) Int. Cl.
*G06K 9/00* (2006.01)
*A61B 5/024* (2006.01)
(Continued)

(52) U.S. Cl.
CPC ........ *A61B 5/02416* (2013.01); *A61B 5/0077* (2013.01); *A61B 5/02108* (2013.01);
(Continued)

(58) Field of Classification Search
CPC ........... G06K 9/00281; G06K 9/00288; G06K 9/00315; A61B 5/02007; A61B 5/0205;
(Continued)

(56) References Cited

U.S. PATENT DOCUMENTS 8,195,460 B2   6/2012  Degani
8,634,701 B2   1/2014  Kang
(Continued)

FOREIGN PATENT DOCUMENTS

EP    3015057 A1    5/2016
EP    3057486 A1    8/2016
(Continued)

OTHER PUBLICATIONS

Savran, Arman, et al. "Emotion detection in the loop from brain signals and facial images." Proceedings of the eNTERFACE 2006 Workshop. 2006.*
(Continued)

*Primary Examiner* — Shefali D Goradia
(74) *Attorney, Agent, or Firm* — Baker Botts L.L.P.

(57) ABSTRACT

In one embodiment, a computer-readable non-transitory storage medium embodies software that is operable when executed to, in real time, capture, by a single sensor, a number of images of a user; determine, based on the number of images, one or more short-term cardiological signals of the user during a period of time; estimate, based on the cardiological signals, a first short-term emotional state of the user; determine, based on the number of images, one or more short-term neurological signals of the user during the period of time; estimate, based on the neurological signals, a second short-term emotional state of the user; compare the first estimated emotional state to the second estimated emotional state; and in response to a determination that the first estimated emotional state corresponds to the second estimated emotional state, determine a short-term emotion of the user during the period of time.

20 Claims, 10 Drawing Sheets

Related U.S. Application Data on May 1, 2017, provisional application No. 62/510,579, filed on May 24, 2017.

(51) Int. Cl.

| | | |
|---|---|---|
| *A61B 5/0452* | (2006.01) | |
| *A61B 5/00* | (2006.01) | |
| *A61B 5/021* | (2006.01) | |
| *A61B 5/16* | (2006.01) | |
| *A61B 5/02* | (2006.01) | |
| *A61B 5/0285* | (2006.01) | |
| *A61B 5/0205* | (2006.01) | |

(52) U.S. Cl.
CPC ........ *A61B 5/02405* (2013.01); *A61B 5/0452* (2013.01); *A61B 5/165* (2013.01); *A61B 5/7221* (2013.01); *G06K 9/00281* (2013.01); *G06K 9/00288* (2013.01); *G06K 9/00302* (2013.01); *G06K 9/00315* (2013.01); *A61B 5/0205* (2013.01); *A61B 5/02007* (2013.01); *A61B 5/0285* (2013.01); *A61B 5/7203* (2013.01); *A61B 5/7235* (2013.01); *A61B 5/7257* (2013.01); *A61B 5/7278* (2013.01); *A61B 2562/04* (2013.01); *G06K 2009/00939* (2013.01); *G06T 2207/30196* (2013.01)

(58) Field of Classification Search
CPC ... A61B 5/0285; A61B 5/7203; A61B 5/7235; A61B 5/7257; A61B 5/7278; A61B 5/02108; A61B 5/02405; A61B 5/0452; A61B 5/165; A61B 5/7221; A61B 5/0077; A61B 5/02416; A61B 2562/04; G06T 2207/30196

See application file for complete search history.

(56) References Cited

U.S. PATENT DOCUMENTS

| | | | | |
|---|---|---|---|---|
| 10,165,949 | B2 * | 1/2019 | Tzvieli | ................ G01J 5/0265 |
| 10,376,153 | B2 * | 8/2019 | Tzvieli | ................ A61B 5/748 |
| 2015/0067708 | A1 * | 3/2015 | Jensen | ............ H04N 21/4756 |
| | | | | 725/10 |
| 2016/0015277 | A1 | 1/2016 | Dumoulin | |
| 2017/0007165 | A1 | 1/2017 | Jain | |
| 2017/0105662 | A1 | 4/2017 | Silawan | |

FOREIGN PATENT DOCUMENTS

| | | |
|---|---|---|
| KR | 101434336 | 8/2014 |
| KR | 101689021 | 12/2016 |
| KR | 101706739 | 2/2017 |
| WO | WO 2005/043453 | 5/2005 |
| WO | WO 2016/193735 | 12/2016 |

OTHER PUBLICATIONS

Extended European Search Report for Application No. 18794775.9, 11 pages, dated Feb. 27, 2020.

Phuong Pham, et al., "Understanding Emotional Responses to Mobile Video Advertisements via Physiological Signal Sensing and Facial Expression Analysis", XP058316918, IUI 2017 Multimodal and Augmented Interaction, Mar. 13-16, 2017, Limassol, Cyprus. pp. 67-78 (12pgs.), Mar. 13, 2017.

Extended European Search Report for Application No. 18794330.3, 8 pages, dated Mar. 20, 2020.

Extended European Search Report for Application No. 18794415.2, 7 pages, dated Mar. 25, 2020.

* cited by examiner

DETERMINING EMOTIONS USING CAMERA-BASED SENSING

PRIORITY

This application claims the benefit, under 35 U.S.C. § 119(e), of U.S. Provisional Patent Application No. 62/500,277 filed 2 May 2017, U.S. Provisional Patent Application No. 62/492,838 filed 1 May 2017, and U.S. Provisional Patent Application No. 62/510,579 filed 24 May 2017, all of which are incorporated herein by reference.

TECHNICAL FIELD

This disclosure generally relates to electronic detection and evaluation of an individual's physiological characteristics.

BACKGROUND

An increasing interest in the evaluation human emotions and/or physiological characteristics, such as cardiovascular health, may be seen in the behavioral, biological, and social sciences. For example, many phenomena, ranging from individual cognitive processing to social and collective behavior, may not be well understood without taking human emotions into account. Recently, there has been an interest in affective computing, which is the study and development of computing systems or devices that can recognize, interpret, process, and simulate human affects. In particular, the emotion of the user may be used as an input for subsequent operations by computing devices or systems. In addition, determining physiological characteristics is useful for detecting or predicting the health of the user.

DESCRIPTION OF EXAMPLE EMBODIMENTS

Figure 1:
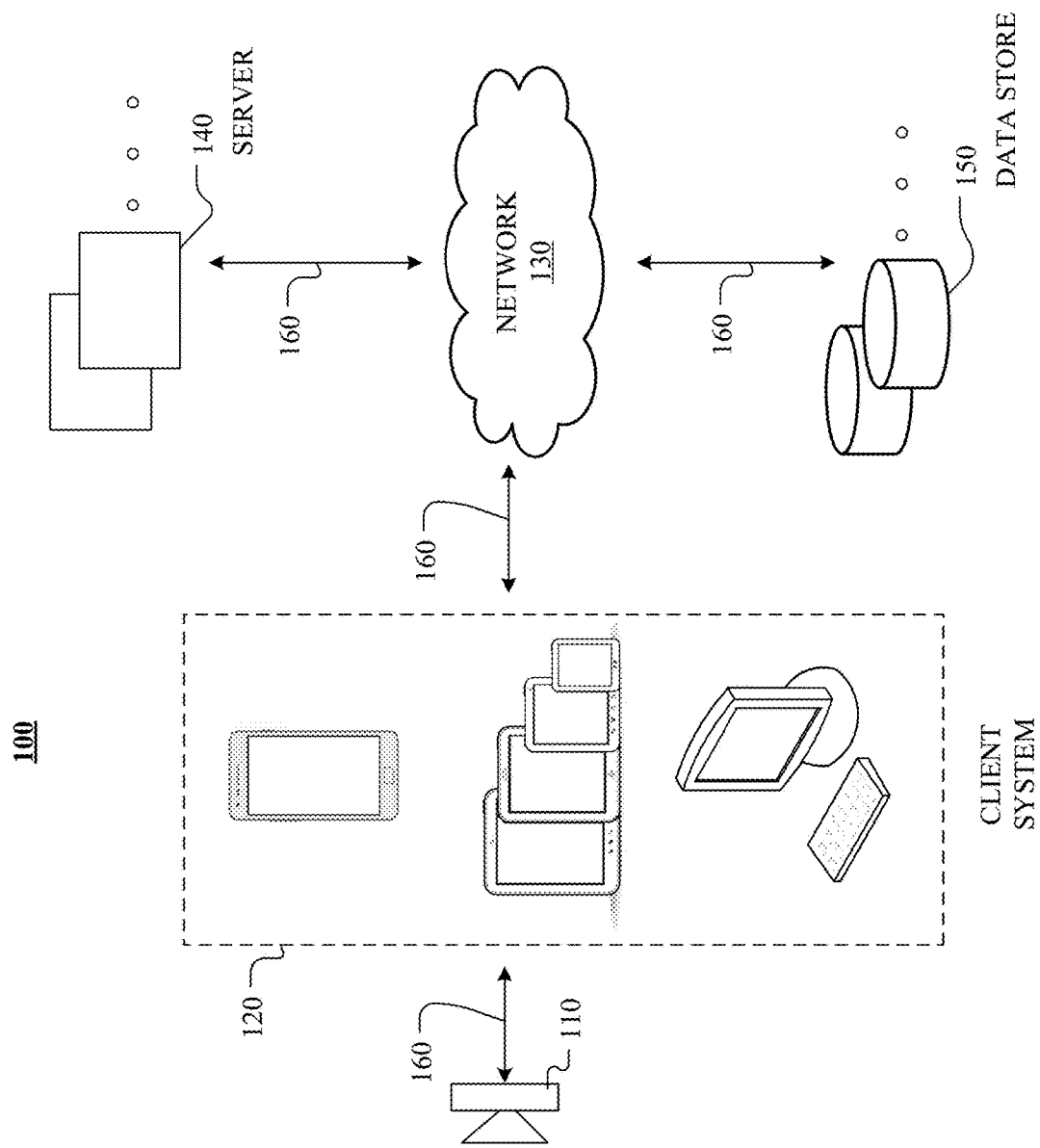
FIG. 1 illustrates an example network environment.
Figure 1:

FIG. 1 illustrates an example network environment 100. Network environment 100 includes one or more optical cameras 110, a client system 120, a network 130, one or more servers 140, and one or more data stores 150. Optical camera 110, client system 120 servers 140, and data stores 150 may be connected to each other by network 130 via links 160. In particular embodiments, optical camera 110 may be integrated with client system 120. Although FIG. 1 illustrates a particular arrangement of optical camera 110, client system 120, network 130, servers 140, and data stores 150, this disclosure contemplates any suitable arrangement of user 110, client system 120, network 130, servers 140, and data stores 150.

Network environment 100 includes one or more optical camera 110 that may be connected to client system 120. In particular embodiments, optical camera 110 is configured to measure data from one or more systems of a human body. As an example and not by way of limitation, optical camera 110 may be configured to monitor cardiological activity of the human body, as described below. As another example, optical camera 110 may be configured to monitor neurological and neuroanatomical activity of the human body, as described below.

In particular embodiments, optical camera 110 may connect to client system 120 directly or via network 130, which may facilitate interaction between and/or transfer of data between optical camera 110 and client system 120. Data (e.g., heart rate, emotional state, etc.) may be stored on client systems 120, data stores 150, other suitable databases, or any combination thereof. In addition, the processing of the data and computations of particular algorithms (as discussed below) may be performed by client system 120, servers 140, other suitable devices/systems, or any combination thereof. In particular embodiments, the processing of the data and computations of particular algorithms may be performed by accessing user data, frame of reference/baseline data, medical data, other relevant data, or any combination thereof, from data stores 150 via network 130.

As an example and not by way of limitation, two or more of client systems 120, servers 140, data stores 150, or any suitable combination thereof may be connected to each other directly (e.g., Ethernet or local area network (LAN) connection), bypassing network 130. As another example, two or more of client system 120, servers 140, and data stores 150 may be physically or logically co-located with each other in whole or in part. In particular embodiments, client system 120 may be any suitable computing device, such as, for example, a mobile computing device, a smartphone, a cellular telephone, a tablet computer, a laptop computer, a personal computer, or any combination thereof. In addition, these devices may communicate with each other via network 130, directly (e.g., by non-network connections), by any other suitable methods, or any combination thereof. As an example and not by way of limitation, client system 120 may communicate with network 130 via a wireless communications protocol, such as Wi-Fi or BLUETOOTH. In particular embodiments, network 130 may be any suitable network. As an example and not by way of limitation, one or more portions of network 130 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 130 may include one or more networks.

In particular embodiments, links 160 may connect client system 120, servers 140, and data stores 150 to network 130 or to each other. This disclosure contemplates any suitable links 160. In particular embodiments, one or more links 160 include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 160 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 160, or a combination of two or more such links 160. Links 160 need not necessarily be the same throughout network environment 100, such that one or more first links 160 may differ in one or more respects from one or more second links 160.

In particular embodiments, servers 140 may be any suitable servers. Each server 140 may be a unitary server or a distributed server spanning multiple computers or multiple datacenters. Servers 140 may be of various types, such as, for example and without limitation, web server, file server, application server, exchange server, database server, proxy server, another server suitable for performing functions or processes described herein, or any combination thereof. In particular embodiments, each server 140 may include hardware, software, or embedded logic components or a combination of two or more such components for carrying out the appropriate functionalities implemented or supported by server 140.

In particular embodiments, data stores 150 may be any suitable data stores. Data stores 150 may be used to store various types of information. In particular embodiments, the information stored in data stores 150 may be organized according to specific data structures. In particular embodiments, each data store 150 may be a relational, columnar, correlation, or other suitable database. Data store 150 may include networked storage such as cloud storage or other network accessible storage. Additionally or alternatively, data store 150 may include local storage within or directly attached to any of the devices of client system 120, such as solid state drives (SSDs) or hard disk drives (HDDs).

In particular embodiments, data store 150 may store various data structures relevant to an optical detection device and the processing of data collected by the optical detection device. As an example and not by way of limitation, data store 150 may store a data structure corresponding to neurocardiology measurements (e.g., measurements of heart rate (HR), heart-rate variability (HRV), data derived from heart rate (HR) or heart-rate variability (HRV) (e.g., sympathovagal balance (SVB)), neurological data, or neuroanatomical data (e.g., lateralization, posture, gestures, or context). As another example and not by way of limitation, data store 150 may store a data structure corresponding to features data and features vectors determined based on a features evaluation process for emotion evaluation. Although this disclosure describes or illustrates particular types of components and uses of these components of network environment 100, this disclosure contemplates any suitable types of components, any suitable network topology (e.g., including a standalone-device topology), and any suitable uses for these components of network environment 100.

Particular embodiments described below describe monitoring and measurement of pathophysiological interplays of the nervous and cardiovascular systems through data collected by optical camera 110. Neurocardiology metrics may be measured in the context of mobile monitoring for use in personalized health evaluation. In mobile monitoring, use of optical camera 110 may facilitate real-time mobile health evaluation. In particular embodiments, neurocardiology metrics may be indicators for various cardiac ailments or conditions. Herein, reference to real-time refers to measurements performed within approximately 5 seconds or less.

The automated evaluation of human emotions is useful in the behavioral, biological, and social applications, among others. Particular embodiments discussed below describe the evaluation of human emotions in the context of mobile monitoring use in personalized entertainment experiences. In mobile monitoring, use of optical camera 110 may facilitate real-time evaluation of human emotions. In particular embodiments, human emotions are evaluated by measuring the activities/arousal of the autonomic nervous system (ANS), where changes in arousal are indicators for various emotions.

Figure 2:
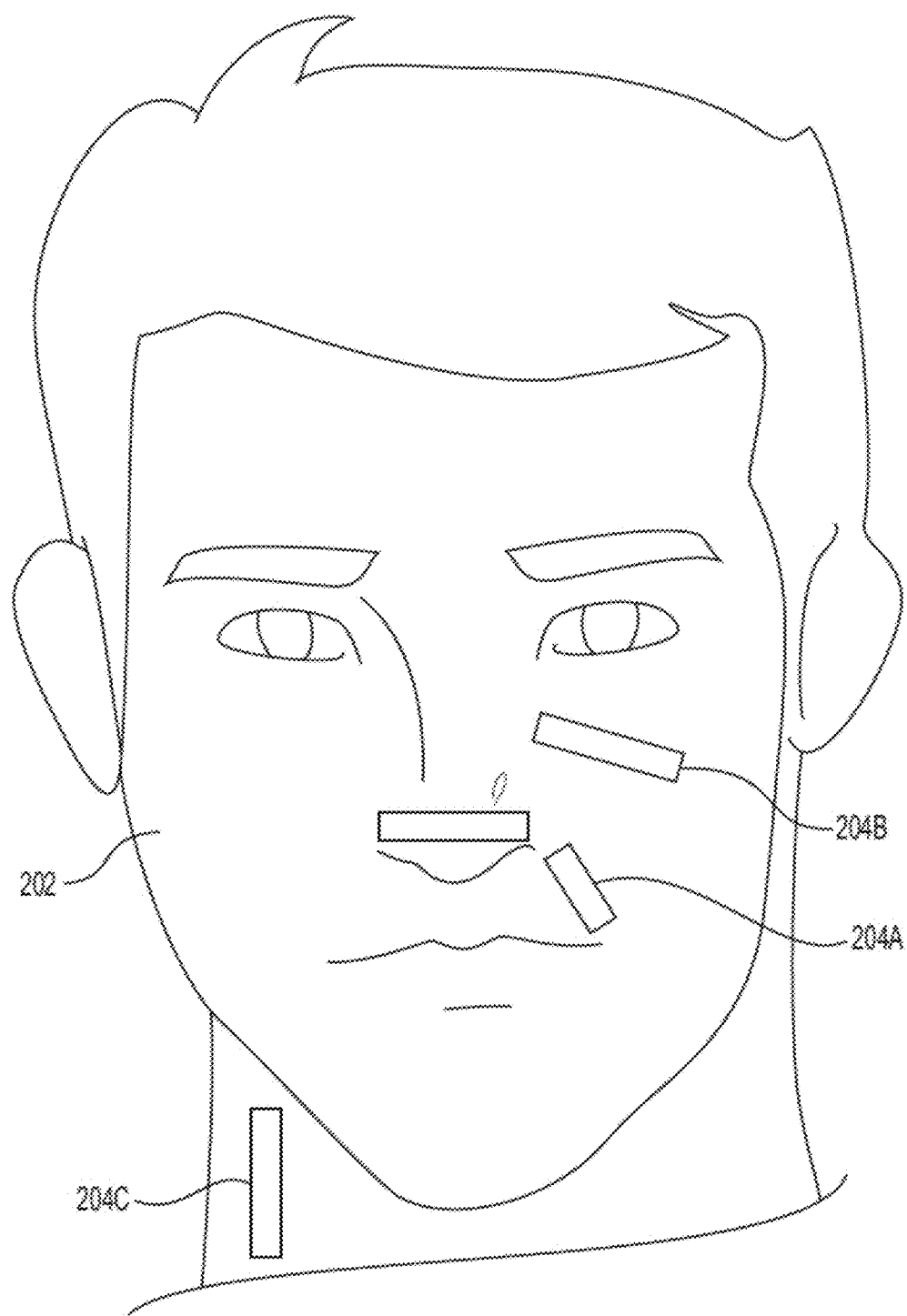
FIG. 2 illustrates example optical measurement areas on the face and neck of a user.

FIG. 2 illustrates example optical measurement areas on the face and neck of a user. In particular embodiments, the optical camera may measure the blood volume with each pulse (BVP) at a particular region of interest (ROI) using photoplethysmogram (PPG). PPG illuminates the skin of a user and determines the underlying cardiovascular activity based on changes in light absorption. As an example and not by way of limitation, PPG may measure a change in blood volume caused by a pressure pulse by illuminating the skin (e.g., by ambient light or from a light-emitting diode (LED) of the optical camera) and measuring the amount of reflected light at particular frequencies using the image sensor of the optical camera. The PPG signal is proportional to the volume of blood in the ROI.

In particular embodiments, PPG measurements may be performed with a focus on the face of the user which is relatively simple to track and has multiple distinctive features (e.g., eyes, mouth, or nose). By using a known layout of arteries on the human body, the blood volume and stiffness analysis may focus on major but superficial (close to the surface) arteries. Superficial arteries are accessible using light with particular wavelengths (e.g., corresponding to the colors red, green, and blue) and a measuring signal modulated by the pulsatile blood in these larger blood vessels may be captured using the optical camera. In particular embodiments, arteries may be selected in advance when the camera is being setup. Images of particular areas of face 202 are captured. As illustrated in the example of FIG. 2, the image of the face 202 of the user may be partitioned by bounding boxes 204A-D that each correspond to a particular ROI. The ROIs may correspond to one or more arteries of face 202. In particular embodiments, data may be extracted from images of the optical camera defined by bounding boxes 204A-D.

By positioning one or more of the bounding boxes 204A-D along known orientations corresponding to particular superficial arteries, a computing system may determine blood volume pulse from fluctuations in the pulsatile blood. A map of several arteries located at varied locations of the face may be created based on the signal quality (e.g., signal strength), such that even when a person is mobile at least one of the arteries may still be located. As an example and not by way of limitation, one or more of the bounding boxes 204A-D may correspond to one or more of the angular, maxillary, ophthalmic, or facial arteries. The superficial arteries may be located using pre-determined human arterial layout information. In particular embodiments, the location of superficial arteries on a particular user's face may be refined during that user's baseline measurements. For example, a device incorporating optical camera 110 (such as a smartphone) may request that the user undergo baseline testing, where the optical camera 110 analyzes and detects superficial arteries in the user's face while the user is looking at optical camera 110. In particular embodiments, one or more of the superficial arteries may be selected based on a signal-to-noise ratio (SNR) associated with the BVP for each of the superficial arteries. As an example and not by way of limitation, the SNR associated with the BVP may be computed by determining the energy in a dominant electromagnetic frequency and its second harmonics as compared to the rest of the signal measured at the ROI. Once arteries are mapped for a given user, then after adjusting for face position or lighting artifacts, the arteries with the highest SNRs may be selected.

Figure 3:
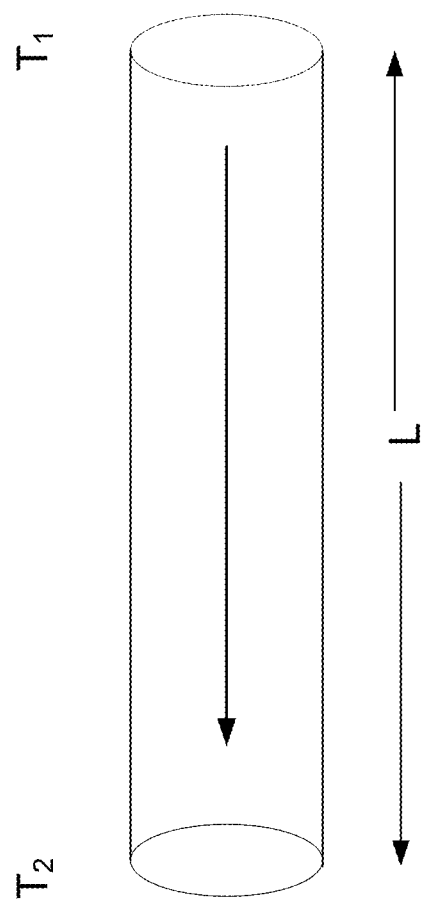
FIG. 3 illustrates an example calculation of cardiological metrics.

FIG. 3 illustrates an example calculation of cardiological metrics. The blood pressure (BP) differs based on the amount of blood which flows through the body at a given instant of time. In particular embodiments, the heart rate or RR-interval may be calculated at an artery location using a blood-volume pulse method. Once an artery is located, as described above, the HR may be determined by analyzing a signal transmission model of blood flow along a length of the selected artery. In particular embodiments, cardiological metrics may be calculated using the blood volume and stiffness associated with the artery. The blood volume may be determined based on calculating the area under the curve (AUC) of the PPG signal. Camera-based pulse wave transit time (PWTT) measurements may detect changes in blood volume, which may be used in structural analysis of the associated artery. PWTT is measure of the amount of time taken by a pulse wave to travel between two points in a circulatory system. As an example and not by way of limitation, the stiffness associated with an artery may be determined based on the PWTT. In the example of FIG. 3, the PWTT and pulse wave velocity may be calculated based on a time difference from an initial time $T_1$ to a final time $T_2$ for blood to flow along a length L of an artery, as illustrated by equations (1) and (2) below.

$$PWTT = T2 - T1 \qquad (1)$$

$$\text{Pulse Wave Velocity} = L/(T2 - T1) \qquad (2)$$

Figure 4:
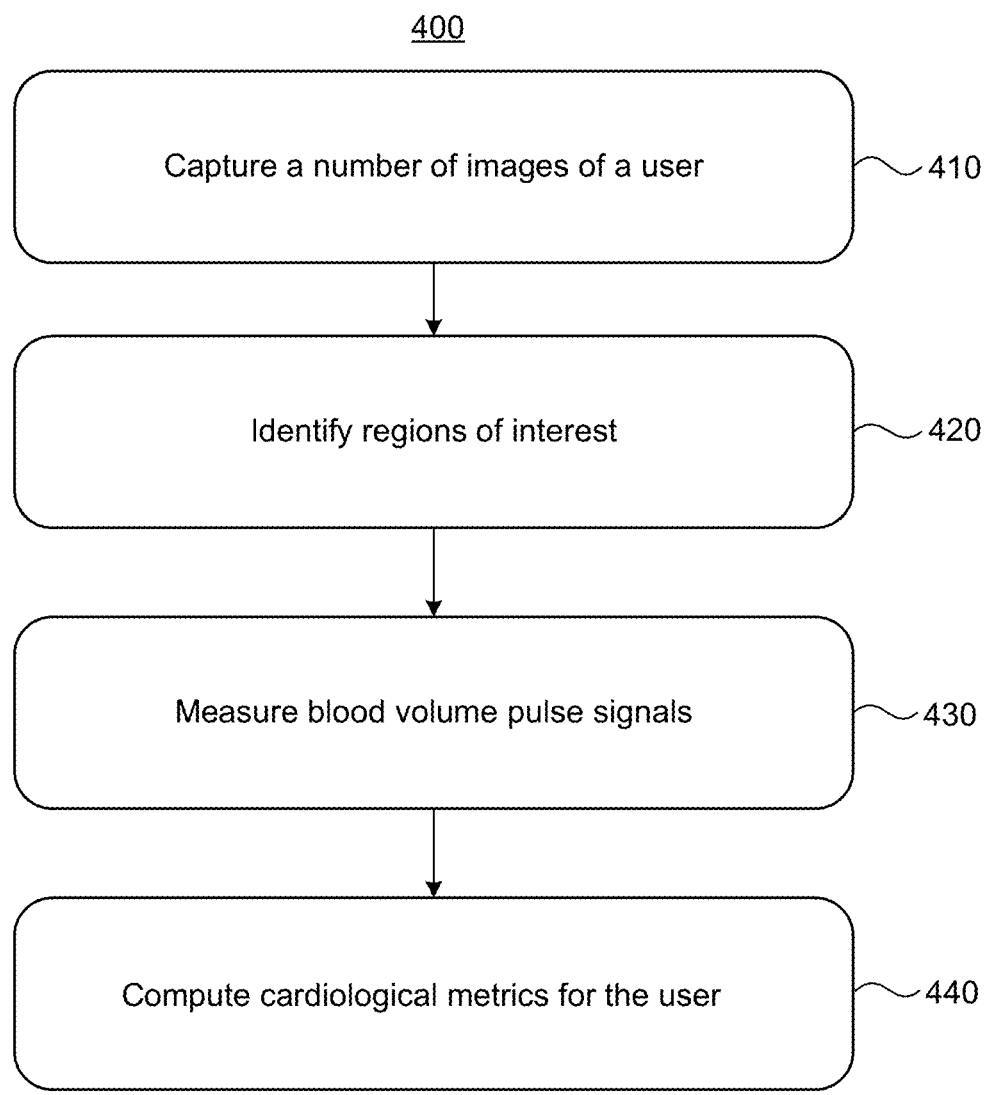
FIG. 4 illustrates an example method for calculating cardiological metrics for a user.

FIG. 4 illustrates an example method for calculating cardiological metrics for a user. As described below, cardiological metrics of the user may be evaluated by correlating the features of brain-wave activity and cardiac activity to particular emotions. The example method 400 may be deployed on one or more electronic devices, such as a mobile phone, tablet computer, mobile devices, fixed-location computing devices, and/or network or cloud deployed systems, having suitable communication, processing, sensing facilities, or any combination thereof. As an example and not by way of limitation, a processor or circuitry may embody the method (e.g., one or more computer processors may be communicatively coupled to a data storage device that stores instructions executable by the one or more computer processors to perform operations of example method 400 for cardiological metric evaluation).

The method 400 begins at step 410, where an optical camera associated with a computing system captures images of a user in real-time. In particular embodiments, the optical camera is attached to or integrated with the computing system. At step 420, one or more regions of interest corresponding to one or more superficial arteries of the user are identified. In particular embodiments, the identification of the superficial arteries is based on the SNR of photoplethysmogram (PPG) data obtained from the captured images. At step 430, the computing system may measure, based on the PPG data, blood volume pulse (BVP) signals. At step 440, based on the measured BVP signals, the computing system can compute one or more cardiological metrics for the user.

Particular embodiments may repeat one or more steps of method 400 of FIG. 4, where appropriate. Although this disclosure describes and illustrates particular steps of the method of FIG. 4 as occurring in a particular order, this disclosure contemplates any suitable steps of the method of FIG. 4 occurring in any suitable order. Moreover, although this disclosure describes and illustrates an example method for calculating cardiological metrics for a user, including the particular steps of the method of FIG. 4, this disclosure contemplates any suitable method for calculating cardiological metrics for a user including any suitable steps, which may include all, some, or none of the steps of the method of FIG. 4, where appropriate. Furthermore, although this disclosure describes and illustrates particular components, devices, or systems carrying out particular steps of the method of FIG. 4, this disclosure contemplates any suitable combination of any suitable components, devices, or systems carrying out any suitable steps of the method of FIG. 4.

In particular embodiments, metrics associated with respiration may be measured using remote PPG (rPPG) to perform concurrent analysis of multiple arteries located on or in a vicinity of the nose. The parasympathetic nervous system is activated by exhalation during respiration. By measuring the movement of blood through the nasal arteries, a number of respiration metrics including inhalation and exhalation time may be determined by measuring blood volume change as well as the periodic motion of the blood flowing through the respective artery. The respiratory rate of the user may be computed using a composite BVP signal. In particular embodiments, the composite BVP signal is a signal based on concurrent measurements of BVP change across multiple superficial nasal arteries. The mechanics of respiration may induce periodic head motions, that in turn modulate the signal (e.g., through reflection) from the nasal arteries. In particular embodiments, the effect of the periodic head motions on the resultant composite BVP signal may be compensated using a measurement of BVP change across a non-nasal artery. As an example and not by way of limitation, the composite BVP signal may be refined using a forehead artery. The arteries of the forehead are free from emotion expressions that may modulate light reflection from the face. Although this disclosure illustrates and describes measuring particular cardiological and respiration metrics using particular types of sensors, this disclosure contemplates the use any suitable types of sensors for measuring cardiological and respiratory metrics.

As described above, one or more cardiological measurements may be calculated based on the physiologically plausible or analyzable sub-segments of the PPG waveform. In particular embodiments, physiologically plausible or analyzable sub-segments may be defined as sub-segments that satisfy a threshold SNR. Features (e.g., peaks, zero crossings, or troughs) of the PPG waveform may be used to find one or more analyzable segments for extracting or calculating cardiological and respiratory metrics. In particular embodiments, analyzable segments may be obtained by analyzing the signal-to-noise ratio (SNR) of the PPG signal with respect to a baseline signal and then computing a noise quotient of the test signal with respect to the dominant signal and its harmonics, depending on whether the underlying processes being captured uses a reflected chrominance signal or a pulmonary blood volume (PBV) signal. In other embodiments, the signal components may be obtained from a theoretical model or from a database and expected frequency components. As described below, a PPG signal profile may be computed to guide pathological cases. As an example and not by way of limitation, in people with arrhythmias, the baseline signal, even if completely noise free, may falsely appear to be a highly corrupted signal.

The PPG waveform extracted from images from the camera is a time series that may be segmented into analyzable sub-segments for finding the HR. In particular embodiments, one or more pre-defined, physiological signal characteristics may be used to identify the analyzable sub-segments of the PPG waveform. In particular embodiments, the BVP and pulse timing may be compared with the expected behavior of a respiratory profile. Valid segments should correspond to characteristics expected out of a measured BVP, such as for example consistency between timing, amplitude, morphology, or respiratory sinus arrhythmia (RSA). Valid cardiac pulses may be extracted through analysis of respiratory variations of PPG waveforms and to identify the PPG waveforms with inconsistent or implausible RR interval (where "RR" refers to the time between heartbeats) or amplitude. Physiologically plausible pulses may conform with characteristics that are expected from BVP measurements. As an example and not by way of limitation, during exhalation the BVP progressively increases while the RR intervals also progressively increases, and the converse is the case during inhalation. The co-occurrence or high covariance between these signals may be an indication of the physiological plausibility of the given waveform.

As another example, analyzable sub-segments of the PPG waveform may correspond to a RR-interval that is consistent with the dominant frequency in the fast Fourier transform (FFT) of the signal. In particular embodiments, the overall time series may be refined using contextual analysis of frequency transform over short time series segments to remove pulses that lead to a HR calculation that is physiologically implausible. In addition, pulse origins of the analyzable time segments must not happen at physiologically implausible points.

Additionally, the profile of the BVP should be consistent with a pre-defined blood pulse, where the rising part (the systolic part) is less than the diastolic part (the decaying part of the pulse). For analyzable segments, the 90% width of the blood pulse should be approximately equal to the RR-interval for cases where there is no pulsatile activity between two signals. As described above, pre-defined signal characteristic is used to identify analyzable sub-segments of the PPG signal that are consistent with a pre-determined respiratory profile that is physiologically plausible. As an example and not by way of limitation, the PPG waveform may be analyzed to determine whether the measured pulse volume measurement progressively increases while R wave-to-R wave (RR) intervals progressively increase during exhalation. Conversely, analyzable sub-segments should have a pulse volume measurement that progressively decreases while RR-intervals progressively decrease during inhalation. In addition, analyzable sub-segments of the PPG signal may be confirmed by determining whether a corresponding systolic part of the signal is less than a corresponding diastolic part of the same signal.

As described above, the PPG waveform extracted from data captured by a camera includes a red, green, and blue channel component. Visible light at different wavelengths, corresponding to different colors of the visible spectrum (e.g., red, green, or yellow), penetrates skin to varying depths depending on its wavelength. In particular embodiments, the PPG waveform may be analyzed to determine whether the signals associated with any of the red, green, or blue channels are physiologically implausible based on pre-determined criteria. As an example and not by way of limitation, one such criterion is based on the DC power of the signal reflected from the face of the user. The power of the reflected signal is inversely proportional to the amount of light absorbed by skin. Human skin may be thought of having two layers, the epidermis and dermis. The epidermis contains melanin, which has a preferential absorption for lower wavelength (blue) light to protect humans from ultraviolet rays. For this reason, a significant portion of the incident blue light does not make it through the epidermis and into the dermis. Therefore the blue component of visible light has the lowest penetration depth, but most of the light is not reflected, but instead is absorbed by the epidermis. Additionally, if blue light penetrates to the dermis, this blue component interacts with hemoglobin (and other cutaneous pigments) and goes through an additional absorption further reducing the amount of reflection. Therefore, the blue component of visible light has the lowest reflectance, such that the signal from the blue channel has the lowest total power of the overall signal.

The red component is the only component reflected at all layers of the skin leading to the red component having the highest penetration depth and total power. In particular embodiments, a PPG segment may be discarded as unreliable or implausible if the total power of the blue component is higher than either the red or green component total power. The DC blue reflectance should be less than the DC reflectance green component, which is less than DC reflectance of the red component. Thus, in analyzable segments of the PPG waveform, the total power of the red components should be greater than the total power of the green components, which should be greater than the total power of the blue components. In particular embodiments, a PPG segment may be discarded as unreliable if it does not conform to this pattern. It should be noted that these criteria are strictly valid under the assumption that the incident light is "white" (approximately equal amounts of each color component (e.g., red, green, and blue) is incident to the skin surface of the user). For example, if a narrow blue-light source was incident to the surface of the human skin, then the criterion above may not be valid. In particular embodiments, this assumption of a "white" light source may be tested using the optical camera while performing baseline measurements.

Another example criterion is based on the AC component of the signal. The AC component of the signal results from the reflectance variation as blood flows (e.g., from the heart beat of the user) through the ROI. In particular embodiments, the captured signal from the camera may be validated based on the pre-defined signal characteristics, as described above. Blood is the main chromophore in the face and causes stronger attenuation then the melanin, and leads to greater absorption of the green component of than the red component. The effect leads to the pulsatile (i.e., AC) power of the green channel to be the largest of the 3 components. As an example and not by way of limitation, a segment may be discarded as unreliable if the pulsatile power of the green component is lower than the pulsatile power of the red or blue channel components. Variations in both the AC and DC components of the captured signal may arise from changes in environmental illumination. These variations from environmental illumination may be compensated (e.g., through measurements of a forehead artery, as described above) or the corresponding segments may be flagged as invalid.

Another example criteria to validate segments of the PPG waveform is based on the covariance of the signal. In particular embodiments, the captured signal from the camera may be validated based on whether the red, green, and blue channel components are co-variant for a particular signal, such that pulses in three channel components are time aligned. As described above, each color channel is mainly modulated by the flow and light absorption from blood. Segments of the signal where the components from the three channels do not have high covariance may be rejected and not used in calculating the relevant cardiological or respiration metrics.

In particular embodiments, segments of the PPG waveform may be rejected on the discrete Fourier transform (DFT) power of the segments. As an example and not by way of limitation, the DFT peak should be consistent with RR or RR-deltas. In particular embodiments, the SNR of the time segments may be considered when comparing the RR values to the DFT peak. As an example and not by way of limitation, particular embodiments check for a suitably high SNR between the narrowband frequency component and the noise floor. If SNR is low, the current window (i.e., PPG sample being analyzed) is discarded. Segments may be discarded or corrected based on observing the values within a time window. In particular embodiments, time segments may be rejected based on a threshold for maximum acceptable median of windowed covariance between normalized mean-centered RGB channels.

As described above, the analyzable segments of the PPG waveform may be used to calculate an average HR or HR range of the user. In a first step, analyzable segments may be identified using co-variance analysis. In particular embodiments, this step may occur during an initialization period. The second step involves subsequent tracking of arteries of interest using images collected from the camera, as described above. In a third step, high valued impulses (e.g., with sharp edges/discontinuities) may be removed or ignored in the HR calculation. In a fourth step, signal transformation may be performed using pixel quotient in log space or blood volume pulse. In a fifth step, signal features (e.g., peak, trough, zero-crossings, signal profile, SNR, etc.) may be used to calculate the RR. In a sixth step, physiologically plausible signal or analyzable segments may be identified based on in the signal R, G, B channels, the total signal power and the total pulsatile power obtained from the images captured by the camera, as described above. Physiologically plausible or analyzable segments may be identified using respiration, blood volume (signal amplitude), and timing variation analysis, as described above. In a next step, implausible pulses may be removed using frequency analysis. Noisy segments in a time series may be identified by comparing the SNR of time series with the baseline signal profile. In particular embodiments, RR is determined based on time-domain analysis using proximal pulses, which is then used to calculate an average HR or HR range. In particular embodiments, the above analysis may be performed using independent component analysis (ICA) of the time series, where the time series is incremented in periodic increments of a pre-determined number of frames, until the mutual information (MI) of the independent components is close to 0. The HR may be calculated by calculating the FFT of the largest independent component.

Figure 5:
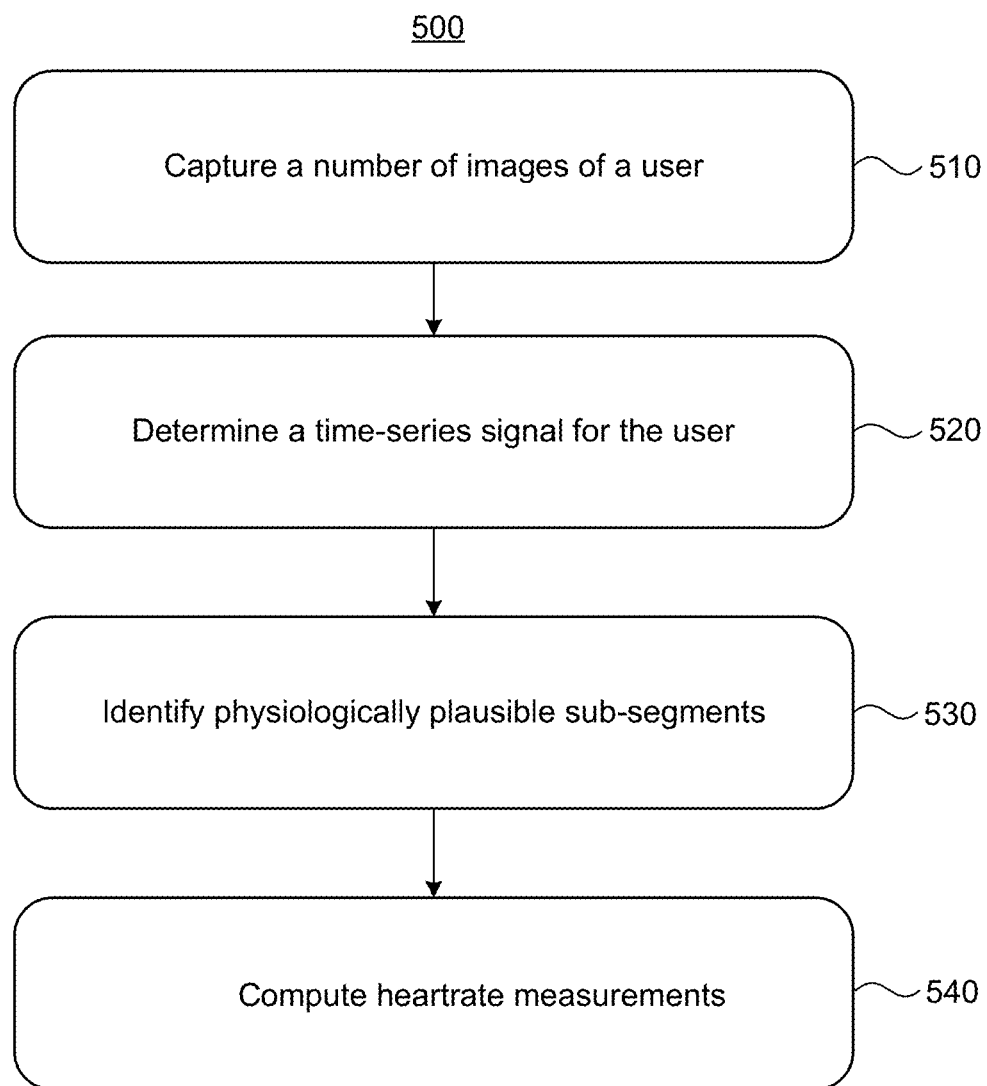
FIG. 5 illustrates an example method for performing heartrate measurements for a user.

FIG. 5 illustrates an example method for performing heartrate measurements for a user. The method 500 begins at step 510, where an optical camera associated with a computing system captures images of a user in real-time. In particular embodiments, the optical camera is attached to or integrated with the computing system. At step 520, the computing system may determine a time-series signal for the user based on the plurality of images. In particular embodiments, the signal includes one or more segments that are physiologically plausible and one or more segments that are physiologically implausible. At step 530, the computing system may identify one or more of the physiologically plausible sub-segments based on one or more pre-defined signal characteristics. In particular embodiments, the identification may include calculating the SNR of the time-series and comparing the SNR to a threshold SNR. Sub-segments of the signal with a calculated SNR that is higher than the threshold SNR may be identified. At step 540, the computing system may calculate one or more heartrate measurements based on the physiologically plausible sub-segments.

Particular embodiments may repeat one or more steps of method 500 of FIG. 5, where appropriate. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates an example method for performing heartrate measurements for a user, including the particular steps of the method of FIG. 5, this disclosure contemplates any suitable method for performing heartrate measurements for a user including any suitable steps, which may include all, some, or none of the steps of the method of FIG. 5, where appropriate. Furthermore, although this disclosure describes and illustrates particular components, devices, or systems carrying out particular steps of the method of FIG. 5, this disclosure contemplates any suitable combination of any suitable components, devices, or systems carrying out any suitable steps of the method of FIG. 5.

The cardiovascular system is regulated by the ANS, that includes the sympathetic nervous system (SNS) and parasympathetic nervous systems (PSNS). Sympathovagal balance (SVB) is defined as the equilibrium point between the SNS and the PSNS. The rhythm of the heart is controlled by the sinoatrial (SA) node, which is modulated by both the sympathetic and parasympathetic branches of the autonomic nervous system. The heart receives its neural input through parasympathetic and sympathetic ganglia and lateral grey column of the spinal column. Sympathetic activity tends to increase heart rate, while parasympathetic activity tends to decrease heart rate. In particular embodiments, SVB-based evaluation of emotions may determine a homeostatic equilibrium where the sympathetic outflow and PSNS (e.g., vagal nerve) outflow are in stable balance. Accordingly, SVB may be determined by analyzing relative dominance and balance between the SNS and PSNS (e.g., between parasympathetic outflow and sympathetic outflow). This approach is linear in nature, which makes it very stable to noise (e.g., which tends to be non-linear in nature).

Figure 6A:
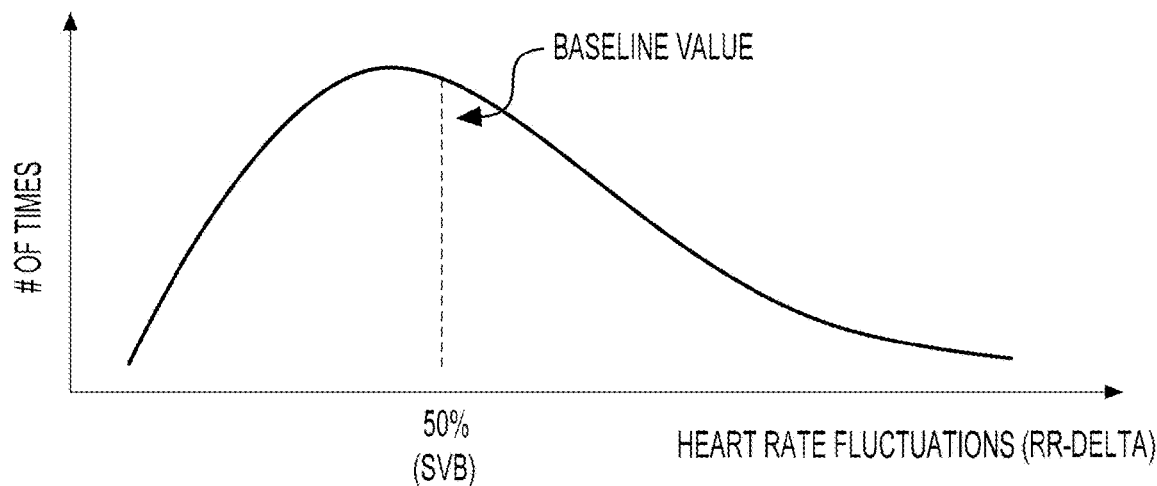
FIG. 6A illustrates an example of a baseline data histogram.

FIG. 6A illustrates an example of baseline data histogram. As illustrated in the example of FIG. 6A, the x-axis of baseline data histogram 600 corresponds to heart rate fluctuations (e.g., RR-deltas or RR interval differences between successive heart beats), and a y-axis of baseline data histogram 600 corresponds to a frequency or number of times particular heart rate fluctuations occur for a set of baseline data. A portion of a set of measurement data that is on one side of the baseline SVB is used to determine a number of ANS activity markers within a first portion of cardiac activity data. A HRV characteristic that is a ratio involving the number of ANS activity markers within the first portion and the number of ANS activity markers within a second portion of the cardiac activity data is calculated. The SVB is defined by the point of 50:50 distribution of baseline data histogram 600 such that 50% of the data points of the set of baseline data are to the left of the SVB and 50% of the data points of the set of baseline data are to the right of the SVB. HRV data is used to determine changes in the SVB. HRV describes the variations between consecutive heartbeats. Using baseline data histogram 600, the SVB corresponds to a HRV zone representative of a "normal" (e.g., non-stressed) state. The analysis of SVB described treats the SNS and PSNS with equal weightage (e.g., because both may be useful in analyzing the ANS arousal) and uses the RR-deltas.

In particular embodiments, to determine SVB, stress or arousal is defined as increased dominance of the SNS in the RR-delta histogram $H_t$ of test data t, and the data points on the histogram correspond to the difference between a length of adjacent RR intervals in a set of test data. In particular embodiments, a ratio of a number of events relatively mapped to SNS with a number of events relatively mapped to PSNS is computed. Measurements of HRV may be based on time-domain analysis or frequency domain analysis, which both have numerous shortcomings. As an example, frequency domain analysis methods such as those based on FFT, are not very suitable for implementation on mobile platforms since they are extremely sensitive to the noise artifacts, and require rather long measurement time periods. Time domain methods, such as root mean square of successive heartbeat interval differences (RMSSD), standard deviation of NN (beat-to-beat) intervals (SDNN), and the proportion of the number of pairs of successive NNs that different by more than 50 milliseconds divided by the total number of NNs (pNN50), are frequently used to analyze the instantaneous heart-rate signal. Given a baseline SVB of the user, and an RR-delta histogram $H_t$, the SVB may be computed as a median of all RR-deltas, a mean value of all RR-deltas, 50% of RMSSD, computed over $H_t$, 50% of SDNN, computed over $H_t$, other relevant values, or any combination thereof.

Figure 6B:
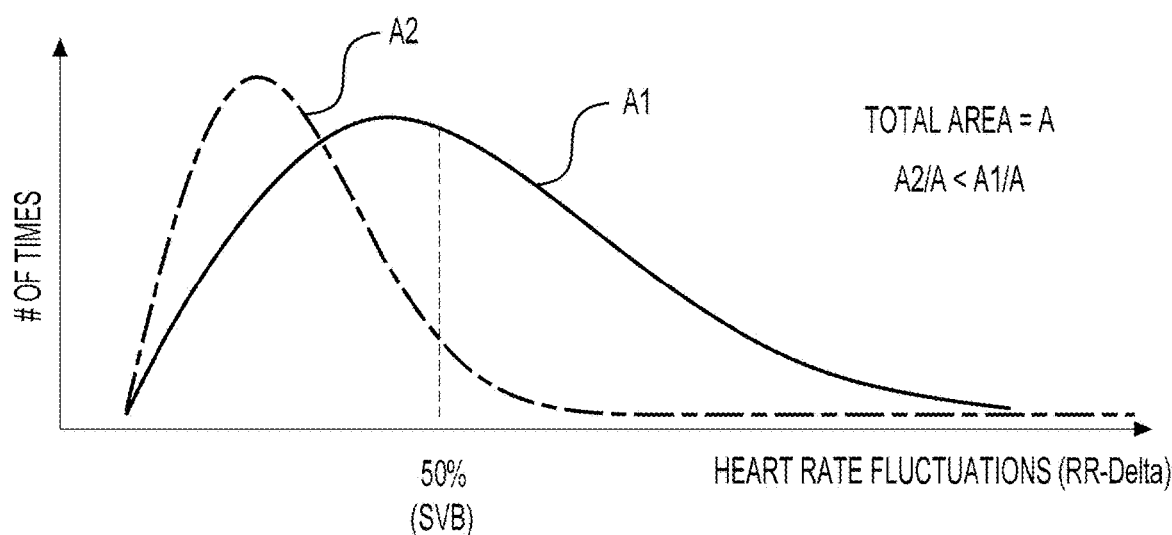
FIG. 6B illustrates an example of a test data histogram in which a sympathovagal balance is shifted to the left.
Figure 6C:
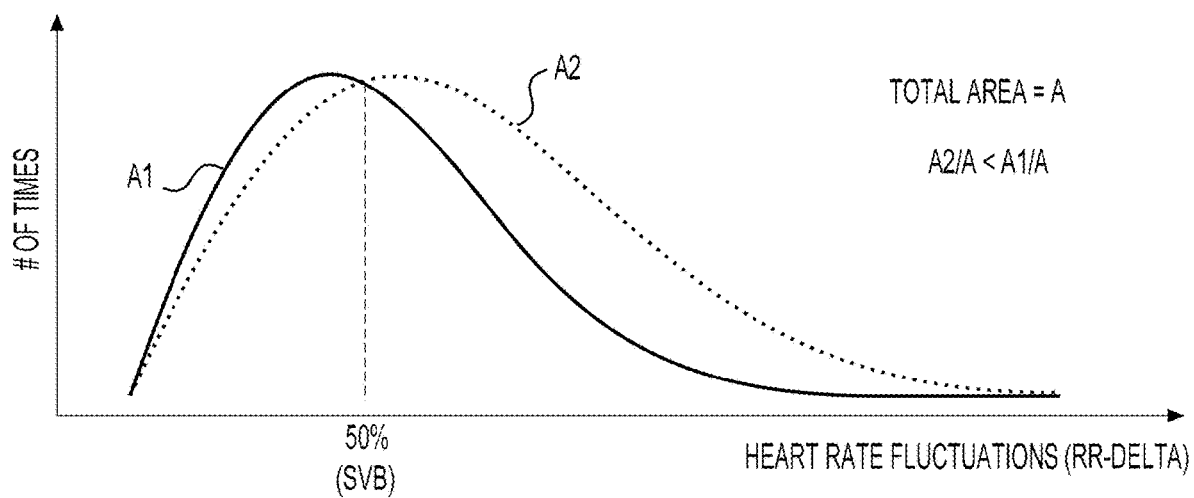
FIG. 6C illustrates an example of a test data histogram in which a sympathovagal balance is shifted to the right.

FIG. 6B illustrates an example of a test-data histogram 610 in which the SVB is shifted to the left, and FIG. 6C illustrates an example of a test-data histogram 620 in which the SVB is shifted to the right. As illustrated in the example of FIG. 6B, similar to FIG. 6A, an x-axis of test data histogram 610 corresponds to heart rate fluctuations (e.g., RR-deltas), and a y-axis of test data histogram 610 corresponds to a number of times of the heart rate fluctuations for a set of test data. In particular embodiments, the first and second portions of the set of measurement data are selected based on a baseline SVB value (e.g., a user-specific baseline SVB value) that divides a histogram representation of the set of measurement data into the first and second portions. When the heart rate fluctuations for the set of test data on average results in the shifting of balance from histogram A1 (e.g., corresponding to the baseline data) toward a left direction to histogram A2, or in other words, the number of measurements of heart rate fluctuations of histogram A2 that are to the left of the SVB (e.g., as determined based on the baseline data) are greater than the number of measurements of heart rate fluctuations of histogram A2 that are to the right of the SVB, then it is determined that the user's state corresponds to a HRV zone representative of a "high arousal" state. Explained another way, as shown in FIG. 6B, given a total area A, the area of A2 over A (e.g., the area under the curve of A2) is determined to be less than the area of A1 over A (e.g., the area under the curve of A1) when the histogram shifts to the left and it is determined that the user's state corresponds to a HRV zone representative of a "high arousal" state or increased SVB.

On the other hand, as shown in FIG. 6C, similar to FIG. 6A, an x-axis of test-data histogram 620 corresponds to heart rate fluctuations (e.g., RR-deltas), and a y-axis of test-data histogram 620 corresponds to a number of times of the heart rate fluctuations for a set of test data. When the heart rate fluctuations for the set of test data on average results in the shifting of balance from histogram A1 (e.g., corresponding to the baseline data) toward a right direction to histogram A2, or in other words, the number of measurements of heart rate fluctuations of histogram A2 that are to the right of the SVB (e.g., as determined based on the baseline data) is greater than the number of measurements of heart rate fluctuations of histogram A2 that are to the left of the SVB, then it is determined that the user's state corresponds to a HRV zone representative of a "low arousal" state. Explained another way, as illustrated in the example of FIG. 6C, given a total area A, the area of A2 over A (e.g., the area under the curve of A2) is determined to be greater than the area of A1 over A (e.g., the area under the curve of A1) when the histogram shifts to the right and it is determined that the user's state corresponds to a HRV zone representative of a "low arousal" state.

Particular embodiments depend on dividing the RR-delta histogram, $H_t$, based on the notion of contextually appropriate SVB. As an example and not by way of limitation, if the context is all the cyclic components responsible for variability in the period of recording, then the ratio for SVB may be evaluated via the SDNN model.

Figure 7:
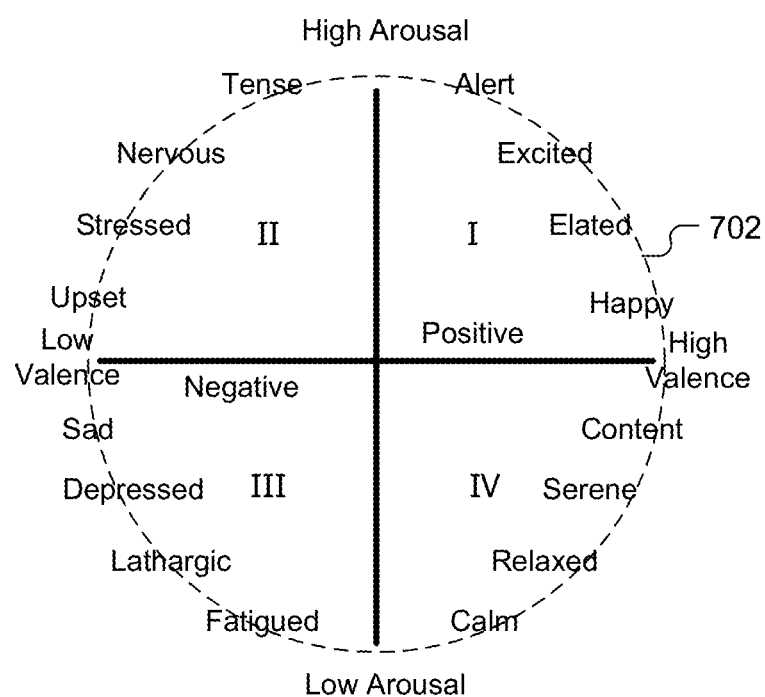
FIG. 7 illustrates an example diagram of the circumplex model of emotion.

FIG. 7 illustrates an example diagram of the circumplex model of emotion. The circumplex model of emotions 700 maps human emotions into a two-dimensional circular space 702 containing arousal and valence dimensions. Levels of arousal are mapped to the vertical axis and the valence is mapped to the horizontal axis of circular space 702. In the circumplex model 700, the valance corresponds to a type of emotion (e.g., positive or negative) while the arousal corresponds to an intensity of the emotion. The center of circular space 702 represents neutral valence and arousal levels. In this model, emotional states can be represented at any level of valence and arousal, or at a neutral level of one or both of these factors. In addition, circular space 702 may be partitioned in four quadrants I-IV that each correspond to a grouping of emotional states with similar levels of arousal and valance. As an example and not by way of limitation, quadrant I emotions correspond to positive valance and high-arousal emotional states. In the illustrated embodiment, emotional states of quadrant I comprise alert, excited, elated, and happy. In order of increasing valence, these emotional states of quadrant I are alert, excited, elated, and happy. In order of increasing arousal, these emotional states of quadrant I are happy, elated, excited, and alert.

Quadrant II emotions correspond to negative valence and high-arousal emotional states. In the illustrated embodiment, emotional states of quadrant II include tense, nervous, stressed, and upset. In order of increasing valence, these emotional states of quadrant II are upset, stressed, nervous, and tense. In order of increasing arousal, these emotional states of quadrant II are upset, stressed, nervous, and tense.

Quadrant III emotions correspond to a negative valance and low-arousal emotional states. In the illustrated embodiment, emotional states of quadrant III include sadness, depression, lethargy, and fatigue. In order of increasing valence, these emotional states of quadrant III can be listed as sadness, depression, lethargy, and fatigue. In order of increasing arousal, these emotional states of quadrant III are fatigue, lethargy, depression, and sadness.

Quadrant IV emotions correspond to positive and low-arousal emotional states. In the illustrated embodiment, emotional states of quadrant IV comprise calm, relaxed, serene, and content. In order of increasing valence, these emotional states of quadrant IV are calm, relaxed, serene, and content. In order of increasing arousal, these emotional states of quadrant IV are calm, relaxed, serene, and content. It will be appreciated that additional emotions can be included, or one or more emotions of FIG. 7 can be omitted or renamed, in alternative example embodiments.

Positive emotions may last for just 10-15 seconds, and so the detection of positive emotions must be performed in a relatively short period of time. In particular embodiments, cardiology-centric analysis to determine emotions of a user may be based on a predictive model of short term emotions by combining linear and non-linear models. As described below, an estimate of the emotions of a user may computed or determined based at least in part on cardiological-based data (e.g., heart rate or SVB) and in conjunction with neuroanatomical or vestibular-somatic reflex data (e.g., posture, gesture, or laterality) measured via an optical camera, such as optical camera 110. In particular embodiments, vestibular-somatic reflex data and simultaneous concordance of cardiological signals may be used to detect a user's emotion, where the cardiological measurements may be determined using a composite model of linear and nonlinear approaches, as described above. As an example and not by way of limitation, the cardiological data may be measured using a linear model for detecting emotion based on the user's sympathovagal balance (SVB). As another example, the cardiological data may be measured using a non-linear model of HR dynamics that is based on heartrate dynamics that converge in approximately 12 seconds. In particular embodiments, the non-linear model is based on a probabilistic-point process non-linear model that may be personalized for the user. This approach models a probability function of the next heartbeat given past events. In particular embodiments, the probability function may be fully parametrized and consider up to cubic auto-regressive Wiener-Volterra relationship to model its first order moment. In other words, these representations may be thought of as convolution of the input signal with a system's impulse response, along with a series of nonlinear terms that contain products of increasing order of the input signal with itself.

In particular embodiments, neurology-centric data may be measured by analyzing the neurological signal that is measured using a facial action coding system (FACS) approach. The FACS approach works by interpreting muscular activities behind the facial expression which is achieved by coding different facial movements into Action Units (AU). These action units are based on the underlying muscular activity that produces the given, and typically, momentary changes in the facial expression. An expression is then recognized by identifying the action unit or the combination of action units which are behind a particular expression. Some of the key parameters used by FACS include eye brows, lip width, mouth, teeth visibility, chin lines, nasolabial lines, nose lines, and/or cheek-based impression of smile lines extracted from the images captured using the camera. FACS is based on more than 30 individual action units that are behind a given facial expression of the user. In particular embodiments, a machine-learning (ML) model, such as for example neural networks, hidden Markov models (HMM), or SVM (support vector machines) may be employed to train the interpretation of the action units extracted from the images of the user captured by the camera. Since genders show emotion differently, the adjusted ML model may be adjusted for gender.

Neuroanatomical or vestibular-somatic reflex (e.g., posture, gesture, or laterality) data may be captured using the optical camera. In particular embodiments, the images captured by the optical camera may be analyzed to determine changes in laterality or posture of the user. As an example and not by way of limitation, the computing system may determine whether a user is experiencing a positive or negative emotion based on laterality since negative emotions may be shown more prominently on left side of the face, while positive emotions may be more prominently shown on the right side of the face. As another example, the computing system may determine whether a user is experiencing a positive or negative emotion based on body posture since bad body posture may be associated with negative emotions, while good body posture may be associated with positive emotions.

Cardiological signals may be determinative of short-term positive emotions if results of both the SVB linear model and heartrate dynamics non-linear model are concurrently sensed and are consistent with a particular emotion. Affective elicitations longer than 6 seconds allow the prefrontal cortex to encode the stimulus information and transmit it to other areas of the central autonomic network (CAN) from the brainstem. Therefore, positive emotions should have a duration of at least 6 seconds plus at least an additional respiratory cycle or more to be detected. The embodiments herein enable detection of an emotional process that lasts somewhere in the vicinity of 10-15 seconds. In particular embodiments, a real-time determination (e.g., within approximately 15 seconds) that the user is experiencing a short-term positive emotion may be further verified using current contextual information associated with the user, including an environment of the user, an activity the user is engaged in, and/or detected physical attributes of the user (e.g., user posture) based at least in part on neurology-centric data, as described above.

In particular embodiments, a computing system may include an emotion-evaluation module. Herein, reference to a module may refer to self-contained computer code or executable that is configured to perform a discrete function. Furthermore, a module may be a dedicated electronic circuit configured to perform the discrete function. The covariance of the RBG channels may be analyzed. In particular embodiments, the computing system computes the HRV-based SVB by analyzing a histogram of HRV measured at pre-determined time intervals (e.g., every 30 seconds), as illustrated in the example of FIGS. 6A-C. As described above, SVB is defined as the equilibrium point between the SNS and the PSNS, therefore the time requirement for accurate SVB calculations is dependent on the stabilization times for the SNS and PSNS measurement. As an example and not by way of limitation, PSNS measurements may take approximately 2 to 3 seconds to stabilize whereas SNS measurements may take approximately 25 seconds. Histograms with larger bins (or longer measurement times) compensate for latency of the system, while smaller bins (or smaller measurement times) may lead to inaccurate SVB calculations. In an example embodiment, SVB and HR are not binary but rather quantify the intensity of SVB and HR activation. Accordingly, the computed intensities can be used to increase the resolution and number of emotional states that can be estimated.

It can take a certain length of time before the brain can process an emotion by higher-order centers of the brain. For example, this time period can be 6 seconds or more. Given the fact that a typical breathing cycle of users is around 4 second per breath which leads to RSA-based variations in HR and HRV and SVB, example embodiments may use a pre-determined time window (e.g., 10 seconds) to affirm the covariant trend from the signals from cardiological data (e.g., from PPG waveform) and neurology-centric data captured from the camera.

Classification is the correlation of an output to a given input (e.g., emotion to neurology-centric and cardiological data). For example, a particular feature vector (e.g., an ordered list of features) may be correlated to a particular emotion of the user. Classification may be performed using a predictor function that is constructed using a set of "training" data that includes an input vector and an answer vector of labeled data. A machine-learning classifier algorithm may combine (e.g., through a dot product) the input vector with one or more weights to construct a predictor function to best fit the input vector to the answer vector. As an example and not by way of limitation, classification algorithms may include support vector machine (SVM), Naive Bayes, Adaptive Boosting (AdaBoost), Random Forest, Gradient Boosting, K-means clustering, Density-based Spatial Clustering of Applications with Noise (DBSCAN), or Neural Network algorithms.

In particular embodiments, during offline training, the training data may be obtained from the neurological (e.g., FACS-based) and cardiological (e.g., HR and SVB) data from a number of users that is captured using the camera and the corresponding emotion of the user at the time the data is being measured. As an example and not by way of limitation, the input vector may be a vector of the extracted neurocardiological features and the answer vector may be the corresponding emotion (e.g., happiness) as reported by the user. As an example and not by way of limitation, training data for emotion evaluation may be images of the users captured while watching a content (e.g., a sports game, TV show, or movie). In particular embodiments, the output vector of the machine-learning classifier may be one or more quadrants or emotions of circumplex model 700 and the output vector may be compared to the answer vector of labeled data (e.g., the user-provided emotion) to "train" the predictor function of the machine-learning classifier.

Facial expressions reflect the effect of brain on the PNS (peripheral nervous system) and the HR/HRV reflect the state of the heart. In particular embodiments, the emotion-evaluation module may receive cardiological and neurological data from images of the user captured by the camera. In particular embodiments, the emotion-evaluation module may be configured to determine emotions of the user based on the covariance of the cardiological and neurological data over a significant period of time (e.g., ~5 or more seconds). In particular embodiments, the emotion-evaluation module may perform an estimation of emotional state of the user during a period of time based on the cardiological data. Moments in time corresponding to pre-determined thresholds of cardiological and neurological data may be used initiate the evaluation of emotions of the user. As an example and not by way of limitation, moments in time corresponding to thresholds (e.g., HRV rising above 60 and a particular facial expression) may be captured and associated with a particular emotion (e.g., elation or excitement). The emotion-evaluation module may include an emotional-state comparison module. In particular embodiments, the emotion-evaluation module may identify emotions based on determining a particular quadrant of the circumplex model of emotion 700 that corresponds to the cardiological and neurological data. As an example and not by way of limitation, the emotion-evaluation module may compute that SVB and HR both increasing at substantially the same time corresponds to quadrant I (upper-right quadrant) of the circumplex model 700, SVB decreasing and HR increasing corresponds to quadrant II (upper left quadrant), SVB and HR both decreasing corresponds to quadrant III (lower-left quadrant), and SVB increasing and HR decreasing corresponds to quadrant IV (lower-right quadrant).

In particular embodiments, the determined emotions of the user may be refined using the neurological data (e.g., posture & activity context-based refinement). As an example and not by way of limitation, decreased SVB and increased HR with a concomitant facial expression may correspond to anger. As another example, decreased SVB and increased HR with a concomitant facial expression may correspond to nervousness. In particular embodiments, the emotion-evaluation module refines the emotion of the user within the particular quadrant of the circumplex model 700 based on the emotion of the user determined by neuroanatomical data (e.g., posture or gestures captured by the camera).

As described above, SVB decreasing and HR increasing is indicative of emotions in quadrant II (e.g., upset, stress, nervous, or tension) of circumplex model 700. In particular embodiments, the analysis of anger is refined through detection of a concomitant detection of bad posture or emotion displayed on the left side of the face. As an example and not by way of limitation, the emotional-state comparison module may estimate the user is feeling elated based determining both SVB and HR increasing, a corresponding facial expression, and at the same time detecting that the user has good posture or the displaying emotion on the right side of the face. As described above, all of the signals necessary to make these determinations may be captured by a signal optical sensor, such as optical camera 110. As used herein, increases and decreases in SVB, and HR levels are relative to baseline values. In particular embodiments, if the trend in the coherence of the neurological and cardiological (in terms of SVB or HR or both) data holds for more than a predetermined amount of time (e.g., 10 seconds), then the computing system may output the estimated emotional state.

Figure 8:
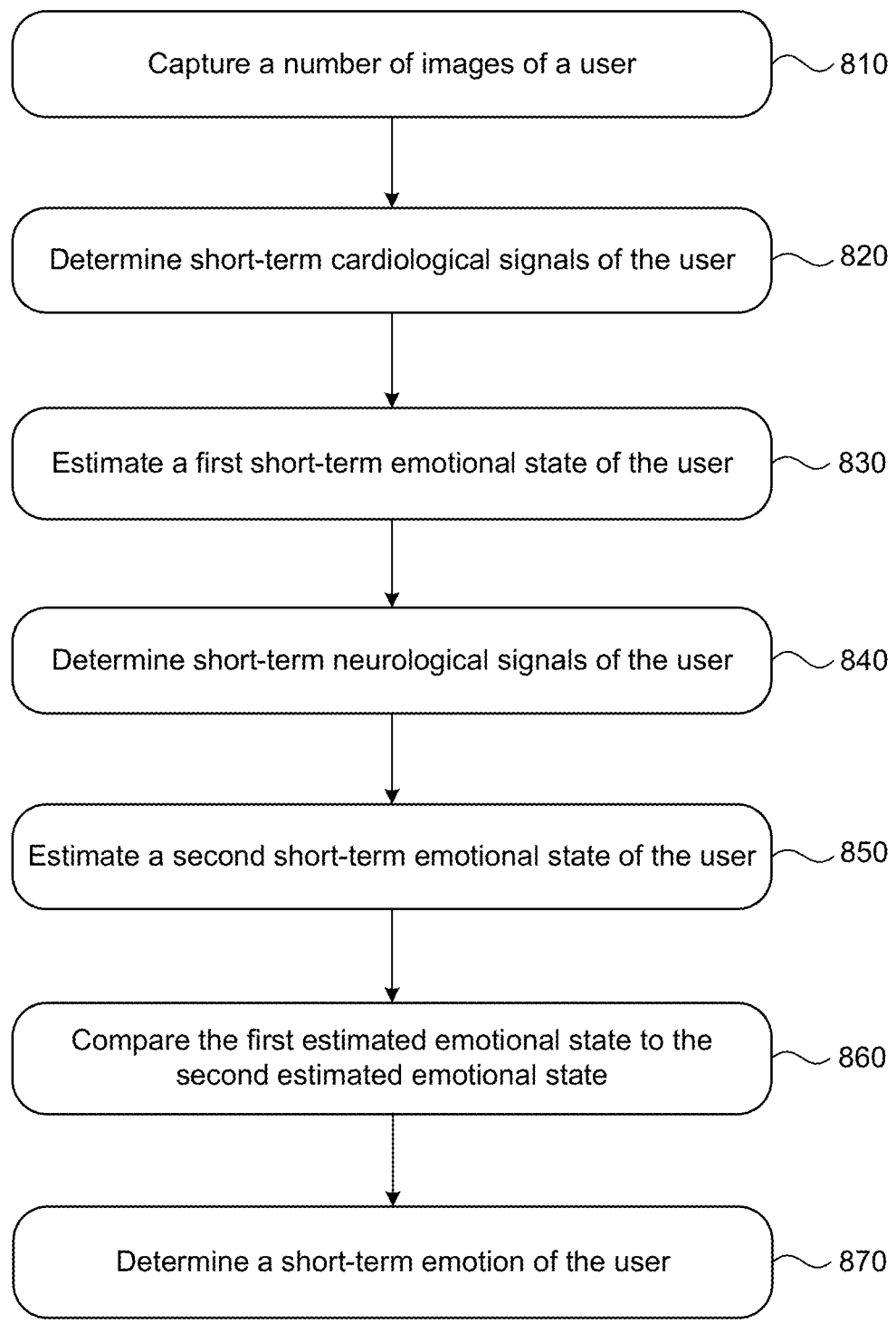
FIG. 8 illustrates an example method for emotion evaluation.

FIG. 8 illustrates an example method for emotion evaluation. As described below, the emotions of the user may be evaluated by correlating the features of brain-wave activity and cardiac activity to particular emotions. In particular embodiments, the method 800 may be performed by an emotion-evaluation system. The method 800 begins at step 810, where a single sensor captures images of a user in real time. At step 820, a computing system determines in real time, based on the captured images, one or more short-term cardiological signals of the user during a period of time. In particular embodiments, at step 830, the computing system may estimate in real-time, based on the cardiological signals, a first short-term emotional state of the user. In particular embodiments, the estimate of the first short-term emotional state is based on the calculated SVB and HR from a PPG waveform extracted from the captured images. In particular embodiments, reference to short-time corresponds to a time period of approximately 15 seconds. At step 840, the computing system may determine in real-time, based on the captured images, one or more short-term neurological signals of the user during the period of time. At step 850, the computing system estimates in real-time, based on the neurological signals, a second short-term emotional state of the user. In particular embodiments, the second short-term emotional state is based on classification of action units, described above, using FACS. At step 860, the computing system may compare the first estimated emotional state to the second estimated emotional state. At step 870, in response to a determination that the first estimated emotional state corresponds to the second estimated emotional state, determine, based on the first estimated emotional state and second estimated emotional state, a short-term emotion of the user during the period of time.

Particular embodiments may repeat one or more steps of method 800 of FIG. 8, where appropriate. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates an example method for evaluating emotions of a user, including the particular steps of the method of FIG. 8, this disclosure contemplates any suitable method for evaluating emotions of a user including any suitable steps, which may include all, some, or none of the steps of the method of FIG. 8, where appropriate. Furthermore, although this disclosure describes and illustrates particular components, devices, or systems carrying out particular steps of the method of FIG. 8, this disclosure contemplates any suitable combination of any suitable components, devices, or systems carrying out any suitable steps of the method of FIG. 8.

In particular embodiments, the embodiments described herein may be used to evaluate the cardiac risk of a user. For example, the determination of atherosclerosis in carotid artery or radial artery may be extremely important in determining the risk of stroke. In particular embodiments, a surrogate marker of blood pressure may be computed using blood volume pulse (BVP) and/or PWTT. As an example and not by way of limitation, determining PWTT across the carotid artery and blood-volume change may enable measurement of an extent of atherosclerosis of a user since arterial stiffness is mediated by the ANS via PWTT. In addition, a stroke risk may be computed based on a measured PWTT across and BVP change in the carotid or radial artery compared with the user's baseline. Similarly, a cardiovascular (CV) hazard may be identified by continuously measuring PWTT across and/or BVP change in one or more of the superficial arteries during a time period during which the user awakens at the time of a morning period.

In particular embodiments, artery mapping may be used to authenticate a user. As described above, facial arteries may be mapped based on the SNR along ROIs of the face of the user using images of the face that are captured by the optical camera. In particular, the angular and supratrochlear arteries are relatively easy to map. This facial-arterial mapping is unique to each user and may serve as a facial signature that may be used as a basis to distinguish between different users. Authentication may be performed using layout of key arteries with respect to facial landmarks (e.g., eyes, nose, ears, or arteries). As an example and not by way of limitation, this facial signature may be captured using the optical camera and stored in a computing system. A user may be authenticated by mapping the key arteries of the user at the time of authentication and compared to the stored facial signature. For example, a user may be authenticated to a device, such as a smartphone or an ATM containing the optical camera.

Accurate detection of emotions may be highly applicable to many fields, such as for example virtual reality (VR), gaming, entertainment, targeted advertisement, smart home, health, or education. Client system 120 may be a computer or smart TV with one or more optical cameras configured to measure neurocardiological and neuroanatomical data of a user. In particular embodiments, the content or a setting associated with content displayed for the user may be adjusted based on the evaluated emotion of the user. As an example and not by way of limitation, a server providing content to the user through a client system may provide a video stream in an interactive way based on the emotion of the user from data captured by the optical camera. For example, a server may provide a video stream while the optical camera may evaluate the emotion of the user. The server may dynamically serve content to evoke a particular emotion. As an example and not by way of limitation, the server may select one or more frames of a video stream that evoke a feeling of relaxation (e.g., cats playing with yarn) for the user and transmit the selected frames for display on a client device. As another example, the client system may pause content if the user is determined to be stressed, angry, or afraid. While this disclosure describes the server or client system as performing a certain action(s), this disclosure contemplates that either client or server device may determine an appropriate action to take based on an evaluation of a user's emotion.

As another example, the server may transmit a video stream corresponding to scenes of a video game for display on a client system (e.g., a computer or smart TV). The server may evaluate the emotion of the user during game play by capturing images of the face of the user and adjust the difficulty level of the game based on the emotion of the user. For example, if the user is expressing frustration during game play, the server may transmit game content having a lower difficulty level. Conversely, the server may transmit game content corresponding to a higher difficulty level based on detecting boredom. As another example, an educational system may determine which content is most engaging to a user and may tailor additional educational content based on what has previously made the user experience positive emotions while learning.

In particular embodiments, the server may send the user one or more recommendations for additional content based on the evaluated emotions of the user while consuming particular content. As an example and not by way of limitation, the server may send a recommendation for similar genres of games (e.g., first-person shooter or social game) based on determining that the user was experiencing happiness or excitement based on facial images captured by the optical camera while playing a particular game. As another example, the server may send a recommendation for a different genre of movies or television shows (e.g., action or sports) based on determining that the user was experiencing depression or fatigue while watching a particular movie or television show.

Figure 9:
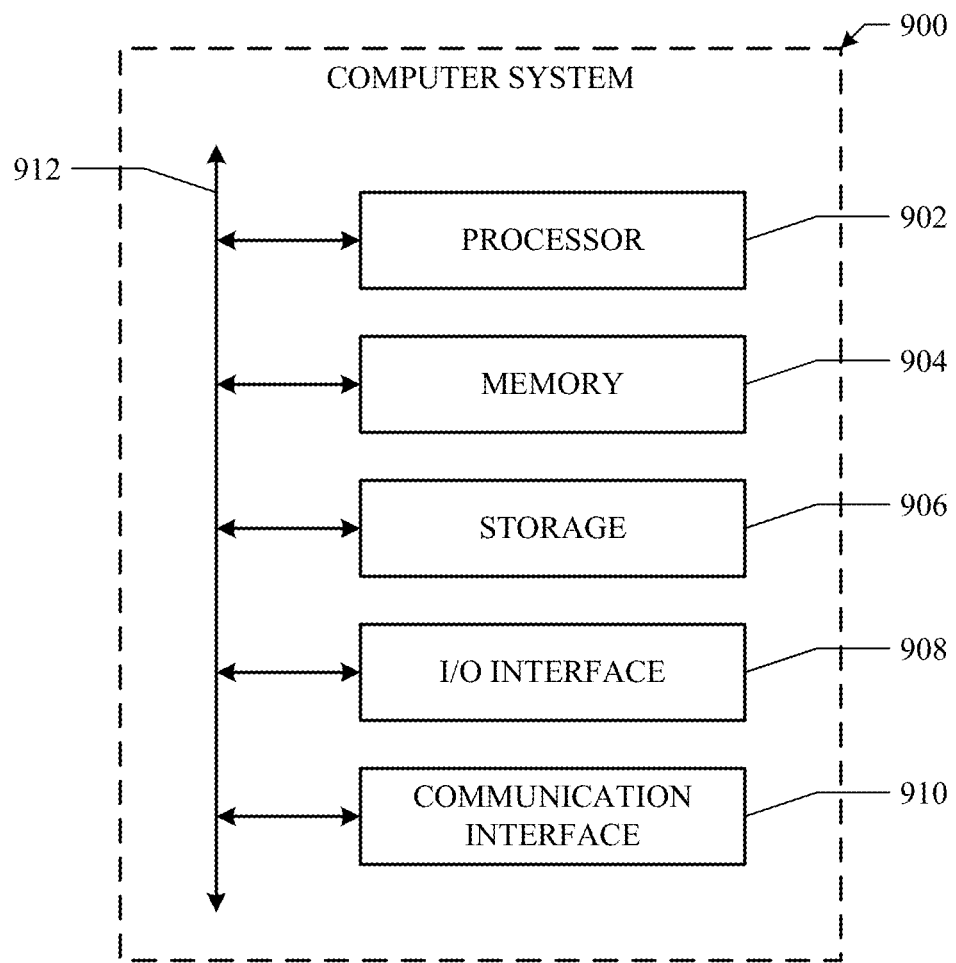
FIG. 9 illustrates an example computer system according to particular embodiments of the invention.

FIG. 9 illustrates an example computer system 900 according to some embodiments of the invention. In particular embodiments, one or more computer systems 900 perform one or more steps of one or more methods described or illustrated herein. In particular embodiments, one or more computer systems 900 provide functionality described or illustrated herein. In particular embodiments, software running on one or more computer systems 900 performs one or more steps of one or more methods described or illustrated herein or provides functionality described or illustrated herein. Particular embodiments include one or more portions of one or more computer systems 900. Herein, reference to a computer system may encompass a computing device, and vice versa, where appropriate. Moreover, reference to a computer system may encompass one or more computer systems, where appropriate.

This disclosure contemplates any suitable number of computer systems 900. This disclosure contemplates computer system 900 taking any suitable physical form. As example and not by way of limitation, computer system 900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 900 may include one or more computer systems 900; be unitary or distributed; span multiple locations; span multiple machines; span multiple data centers; or reside in a cloud, which may include one or more cloud components in one or more networks. Where appropriate, one or more computer systems 900 may perform without substantial spatial or temporal limitation one or more steps of one or more methods described or illustrated herein. As an example and not by way of limitation, one or more computer systems 900 may perform in real time or in batch mode one or more steps of one or more methods described or illustrated herein. One or more computer systems 900 may perform at different times or at different locations one or more steps of one or more methods described or illustrated herein, where appropriate.

In particular embodiments, computer system 900 includes a processor 902, memory 904, storage 906, an input/output (I/O) interface 908, a communication interface 910, and a bus 912. Although this disclosure describes and illustrates a particular computer system having a particular number of particular components in a particular arrangement, this disclosure contemplates any suitable computer system having any suitable number of any suitable components in any suitable arrangement.

In particular embodiments, processor 902 includes hardware for executing instructions, such as those making up a computer program. As an example and not by way of limitation, to execute instructions, processor 902 may retrieve (or fetch) the instructions from an internal register, an internal cache, memory 904, or storage 906; decode and execute them; and then write one or more results to an internal register, an internal cache, memory 904, or storage 906. In particular embodiments, processor 902 may include one or more internal caches for data, instructions, or addresses. This disclosure contemplates processor 902 including any suitable number of any suitable internal caches, where appropriate. As an example and not by way of limitation, processor 902 may include one or more instruction caches, one or more data caches, and one or more translation lookaside buffers (TLBs). Instructions in the instruction caches may be copies of instructions in memory 904 or storage 906, and the instruction caches may speed up retrieval of those instructions by processor 902. Data in the data caches may be copies of data in memory 904 or storage 906 for instructions executing at processor 902 to operate on; the results of previous instructions executed at processor 902 for access by subsequent instructions executing at processor 902 or for writing to memory 904 or storage 906; or other suitable data. The data caches may speed up read or write operations by processor 902. The TLBs may speed up virtual-address translation for processor 902. In particular embodiments, processor 902 may include one or more internal registers for data, instructions, or addresses. This disclosure contemplates processor 902 including any suitable number of any suitable internal registers, where appropriate. Where appropriate, processor 902 may include one or more arithmetic logic units (ALUs); be a multi-core processor; or include one or more processors 902. Although this disclosure describes and illustrates a particular processor, this disclosure contemplates any suitable processor.

In particular embodiments, memory 904 includes main memory for storing instructions for processor 902 to execute or data for processor 902 to operate on. As an example and not by way of limitation, computer system 900 may load instructions from storage 906 or another source (such as, for example, another computer system 900) to memory 904. Processor 902 may then load the instructions from memory 904 to an internal register or internal cache. To execute the instructions, processor 902 may retrieve the instructions from the internal register or internal cache and decode them. During or after execution of the instructions, processor 902 may write one or more results (which may be intermediate or final results) to the internal register or internal cache. Processor 902 may then write one or more of those results to memory 904. In particular embodiments, processor 902 executes only instructions in one or more internal registers or internal caches or in memory 904 (as opposed to storage 906 or elsewhere) and operates only on data in one or more internal registers or internal caches or in memory 904 (as opposed to storage 906 or elsewhere). One or more memory buses (which may each include an address bus and a data bus) may couple processor 902 to memory 904. Bus 912 may include one or more memory buses, as described below. In particular embodiments, one or more memory management units (MMUs) reside between processor 902 and memory 904 and facilitate accesses to memory 904 requested by processor 902. In particular embodiments, memory 904 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 904 may include one or more memories 904, where appropriate. Although this disclosure describes and illustrates particular memory, this disclosure contemplates any suitable memory.

In particular embodiments, storage 906 includes mass storage for data or instructions. As an example and not by way of limitation, storage 906 may include a hard disk drive (HDD), a floppy disk drive, flash memory, an optical disc, a magneto-optical disc, magnetic tape, or a Universal Serial Bus (USB) drive or a combination of two or more of these. Storage 906 may include removable or non-removable (or fixed) media, where appropriate. Storage 906 may be internal or external to computer system 900, where appropriate. In particular embodiments, storage 906 is non-volatile, solid-state memory. In particular embodiments, storage 906 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 906 taking any suitable physical form. Storage 906 may include one or more storage control units facilitating communication between processor 902 and storage 906, where appropriate. Where appropriate, storage 906 may include one or more storages 906. Although this disclosure describes and illustrates particular storage, this disclosure contemplates any suitable storage.

In particular embodiments, I/O interface 908 includes hardware, software, or both, providing one or more interfaces for communication between computer system 900 and one or more I/O devices. Computer system 900 may include one or more of these I/O devices, where appropriate. One or more of these I/O devices may enable communication between a person and computer system 900. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 908 for them. Where appropriate, I/O interface 908 may include one or more device or software drivers enabling processor 902 to drive one or more of these I/O devices. I/O interface 908 may include one or more I/O interfaces 908, where appropriate. Although this disclosure describes and illustrates a particular I/O interface, this disclosure contemplates any suitable I/O interface.

In particular embodiments, communication interface 910 includes hardware, software, or both providing one or more interfaces for communication (such as, for example, packet-based communication) between computer system 900 and one or more other computer systems 900 or one or more networks. As an example and not by way of limitation, communication interface 910 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 910 for it. As an example and not by way of limitation, computer system 900 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 900 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 900 may include any suitable communication interface 910 for any of these networks, where appropriate. Communication interface 910 may include one or more communication interfaces 910, where appropriate. Although this disclosure describes and illustrates a particular communication interface, this disclosure contemplates any suitable communication interface.

In particular embodiments, bus 912 includes hardware, software, or both coupling components of computer system 900 to each other. As an example and not by way of limitation, bus 912 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 912 may include one or more buses 912, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. One or more computer-readable non-transitory storage media embodying software that is operable when executed to, in real time:
   capture, by one or more optical cameras, a plurality of images of a user's face;
   determine, based on a first analysis of the plurality of images of the user's face, one or more short-term cardiological signals of the user during a period of time;
   estimate, based on the cardiological signals, a first short-term emotional state of the user;
   determine, based on a second analysis of the plurality of images of the user's face, one or more short-term neurological signals of the user during the period of time;

estimate, based on the neurological signals, a second short-term emotional state of the user;

compare the first estimated emotional state to the second estimated emotional state; and in response to a determination that the first estimated emotional state corresponds to the second estimated emotional state, determine, based on the first estimated emotional state and second estimated emotional state, a short-term emotion of the user during the period of time.

2. The media of claim 1, wherein the software is further operable to:

detect the face of the user in the plurality of images of the user's face;

determine, based on photoplethysmogram (PPG) data obtained from the plurality of images of the user's face, one or more of the short-term cardiological signals of the user;

determine, based on facial action coding system (FACS) data obtained from the plurality of images of the user's face, one or more of the short-term neurological signals of the user;

determine, one or more neuroanatomical signals of the user based on the plurality of images of the user's face; and confirm the short-term emotion of the user based on a consistency between the neuroanatomical signals and the short-term emotion.

3. The media of claim 2, wherein the FACS data is based on detected characteristics of the user's eye brow, lip width, mouth, teeth visibility, chin lines, nasolabial lines, nose lines, or cheek-based impression of smile lines.

4. The media of claim 2, wherein one or more of the neuroanatomical signals are detected physical attributes of the user.

5. The media of claim 1, wherein the software is further operable to determine one or more of the cardiological signals using a linear model based on a sympathovagal balance (SVB) of the user.

6. The media of claim 5, wherein the software is further operable to:

determine one or more of the cardiological signals using a non-linear statistical model based on heartrate dynamics; and determine that the short-term emotion corresponds to a positive emotion based on concurrently sensing the SVB and heartrate dynamics and based on determining that the SVB and the heartrate dynamics are consistent with positive emotion.

7. The media of claim 1 wherein the determination of the cardiological and neurological signals are performed concurrently.

8. A method comprising, in real time:

capturing, by one or more optical cameras, a plurality of images of a user's face;

determining, based on a first analysis of the plurality of images of the user's face, one or more short-term cardiological signals of the user during a period of time;

estimating, based on the cardiological signals, a first short-term emotional state of the user;

determining, based on a second analysis of the plurality of images of the user's face, one or more short-term neurological signals of the user during the period of time;

estimating, based on the neurological signals, a second short-term emotional state of the user;

comparing the first estimated emotional state to the second estimated emotional state; and in response to a determination that the first estimated emotional state corresponds to the second estimated emotional state, determining, based on the first estimated emotional state and second estimated emotional state, a short-term emotion of the user during the period of time.

9. The method of claim 8, further comprising:

detecting the face of the user in the plurality of images of the user's face;

determining, based on photoplethysmogram (PPG) data obtained from the plurality of images of the user's face, one or more of the short-term cardiological signals of the user;

determining, based on facial action coding system (FACS) data obtained from the plurality of images of the user's face, one or more of the short-term neurological signals of the user;

determining, one or more neuroanatomical signals of the user based on the plurality of images of the user's face; and confirming the short-term emotion of the user based on a consistency between the neuroanatomical signals and the short-term emotion.

10. The method of claim 9, wherein the FACS data is based on detected characteristics of the user's eye brow, lip width, mouth, teeth visibility, chin lines, nasolabial lines, nose lines, or cheek-based impression of smile lines.

11. The method of claim 9, wherein one or more of the neuroanatomical signals are detected physical attributes of the user.

12. The method of claim 8, wherein the determination of one or more of the cardiological signals comprises using a linear model based on a sympathovagal balance (SVB) of the user.

13. The method of claim 12, further comprising:

determining one or more of the cardiological signals using a non-linear statistical model based on heartrate dynamics; and determining that the short-term emotion corresponds to a positive emotion based on concurrently sensing the SVB and heartrate dynamics and based on determining that the SVB and the heartrate dynamics are consistent with positive emotion.

14. The method of claim 8, further comprising concurrently performing the determination of the cardiological and neurological signals.

15. A system comprising:

one or more processors; and a non-transitory memory coupled to the processors comprising instructions executable by the processors, the processors operable when executing the instructions to, in real-time:

capture, by one or more optical cameras, a plurality of images of a user's face;

determine, based on a first analysis of the plurality of images of the user's face, one or more short-term cardiological signals of the user during a period of time;

estimate, based on the cardiological signals, a first short-term emotional state of the user;

determine, based on a second analysis of the plurality of images of the user's face, one or more short-term neurological signals of the user during the period of time;

estimate, based on the neurological signals, a second short-term emotional state of the user;

compare the first estimated emotional state to the second estimated emotional state; and in response to a determination that the first estimated emotional state corresponds to the second estimated emotional state, determine, based on the first estimated emotional state and second estimated emotional state, a short-term emotion of the user during the period of time.

16. The system of claim 15, wherein the processors are further operable to:

detect the face of the user in the plurality of images of the user's face;

determine, based on photoplethysmogram (PPG) data obtained from the plurality of images of the user's face, one or more of the short-term cardiological signals of the user;

determine, based on facial action coding system (FACS) data obtained from the plurality of images of the user's face, one or more of the short-term neurological signals of the user;

determine, one or more neuroanatomical signals of the user based on the plurality of images of the user's face; and confirm the short-term emotion of the user based on a consistency between the neuroanatomical signals and the short-term emotion.

17. The system of claim 16, wherein the FACS data is based on detected characteristics of the user's eye brow, lip width, mouth, teeth visibility, chin lines, nasolabial lines, nose lines, or cheek-based impression of smile lines.

18. The system of claim 16, wherein one or more of the neuroanatomical signals are detected physical attributes of the user.

19. The system of claim 15, wherein the processors are further operable to determine one or more of the cardiological signals using a linear model based on a sympathovagal balance (SVB) of the user.

20. The system of claim 19, wherein the processors are further operable to:

determine one or more of the cardiological signals using a non-linear statistical model based on heartrate dynamics; and determine that the short-term emotion corresponds to a positive emotion based on concurrently sensing the SVB and heartrate dynamics and based on determining that the SVB and the heartrate dynamics are consistent with positive emotion.

* * * * *